US006125292A

United States Patent [19]

Uenoyama et al.

[11] Patent Number: 6,125,292

[45] Date of Patent: Sep. 26, 2000

[54] SENSOR AND A SET OF SENSORS

[75] Inventors: Harumi Uenoyama, Osaka; Kohei Ishida, Shiga, both of Japan

[73] Assignee: Kyoto Daiichi Kagaku Co., Ltd., Kyoto, Japan

[21] Appl. No.: 09/206,581

[22] Filed: Dec. 7, 1998

[30] Foreign Application Priority Data

Dec. 17, 1997 [JP] Japan .................................... 9-348320

[51] Int. Cl.[7] .............................. A61B 5/05; G01N 27/26

[52] U.S. Cl. ............................................ 600/345; 204/403

[58] Field of Search .................................... 600/345, 346, 600/347, 348, 365, 309; 204/403, 400

[56] References Cited

U.S. PATENT DOCUMENTS

| | | | |
|---|---|---|---|
| 3,620,676 | 11/1971 | Davis . | |
| 4,065,263 | 12/1977 | Woodbridge, III . | |
| 4,088,448 | 5/1978 | Lilja et al. . | |
| 4,195,526 | 4/1980 | Amos et al. . | |
| 4,624,928 | 11/1986 | Qureshi . | |
| 4,650,662 | 3/1987 | Goldfinger et al. . | |
| 5,120,420 | 6/1992 | Nankai et al. | 204/403 |
| 5,192,415 | 3/1993 | Yoshioka et al. | 204/403 |
| 5,262,037 | 11/1993 | Markle et al. | 204/415 |
| 5,264,103 | 11/1993 | Yoshioka et al. | 204/403 |
| 5,310,471 | 5/1994 | Markle et al. | 204/415 |
| 5,354,448 | 10/1994 | Markle et al. | 204/415 |
| 5,387,327 | 2/1995 | Khan | 204/403 |
| 5,496,846 | 3/1996 | Khan | 600/347 |
| 5,575,895 | 11/1996 | Ikeda et al. | 204/403 |
| 5,582,697 | 12/1996 | Ikeda et al. | 204/403 |

FOREIGN PATENT DOCUMENTS

| | | |
|---|---|---|
| 57-132900 | 8/1982 | Japan . |
| 1-291153 | 11/1989 | Japan . |
| 4-188065 | 7/1992 | Japan . |
| 7-167820 | 7/1995 | Japan . |
| 8-114539 | 5/1996 | Japan . |
| 10-132712 | 5/1998 | Japan . |
| 2 090 659 | 7/1982 | United Kingdom . |
| WO 96/00614 | 1/1996 | WIPO . |

OTHER PUBLICATIONS

Copy of European Search Report for EP 98 30 6900 dated Jan. 31, 2000.

*Primary Examiner*—Cary O'Connor
*Assistant Examiner*—Navin Natnithithadha
*Attorney, Agent, or Firm*—Merchant & Gould P.C.

[57] ABSTRACT

A sensor includes an analyzing part and a passage having two ends. One end of the passage is connected to the analyzing part. The other end of the passage is closed before use so that the inside of the passage and the analyzing part is sealed to prevent a contact with the outside. When the sensor is to be used, the other end of the passage is opened so as to provide an inlet for a sample.

14 Claims, 6 Drawing Sheets

SENSOR AND A SET OF SENSORS

BACKGROUND OF THE INVENTION

1. Field of the Invention

The present invention relates to a sensor and a set of sensors for use, for example, in measurement of a liquid sample of an organism.

2. Description of the Prior Art

Conventionally, a disposable sensor has been used for general purposes in the field of clinical tests such as biochemical analysis (e.g., Japanese Laid-Open Patent Publication No. 4-188065 and Japanese Patent Publication No. 6-58338). A disposable sensor does not need cleaning after measurement, so that it is suitable for personal use. In particular, a sensor having a capillary passage easily used with a liquid sample such as blood is advantageous for self-monitoring such as self-measurement of blood glucose. Such a sensor can be categorized into two types, i.e., electrochemical type and optical type, which are different from each other in the detecting means.

An electrochemical sensor is provided with, for example, electrodes arranged on a rectangular substrate and a passage through which a sample flows. An end of the passage constitutes an inlet for a sample. A reagent that is changed electrochemically when it reacts with the sample is generally placed on the electrodes. When a sample such as blood is contacted with the sample inlet, the sample is drawn through the passage into an electrode part (analyzing part) by capillary phenomenon, and the sample reacts with the reagent. A component of the sample can be analyzed in the following manner. This sensor is positioned in a measuring device, a sample is supplied, and a voltage is applied to the electrodes. Then, a reaction with the reagent is detected by the electrodes as an electrochemical change.

In an optical sensor, instead of the electrodes and the reagent that effects an electrochemical change, a reagent that effects an optical change when it reacts with a sample is placed on the substrate. A part of the sensor is externally observable by being transparent so that the optical change is detected outside the sensor. Other than that, the optical sensor has the same configuration as that of the electrochemical sensor. The optical change of the reagent is measured by visual observation, a spectrophotometer, a reflectometer or the like. In this manner, a component of the sample is analyzed.

High precision in measurement is required for such a sensor. Therefore, the sensor is prevented from being in contact with the outside, for example, by being contained in a can or closely packaged with an aluminum foil seal one by one, in order to ensure temporal stability of a reagent containing enzyme or to prevent a substance that could interfere with measurement from entering the sensor. However, the containment in a can or the packaging with seals increases the number of steps for production of the sensor, thus leading to high cost. In addition, the containment or the packaging deteriorates the operability of the sensor when it is used.

SUMMARY OF THE INVENTION

Therefore, with the foregoing in mind, it is the object of the present invention to provide a sensor or a set of sensors that are protected against a substance that could interfere with measurement or could deteriorate the sensors, have temporal stability, permit high production efficiency, and have excellent operability.

In order to achieve the above object, the present invention provides a first sensor and a second sensor described as follows.

A first sensor of the present invention includes an analyzing part and a passage having two ends. One end of the passage is connected to the analyzing part. The other end of the passage is closed before use so that the inside of the passage and the analyzing part are sealed to prevent contact with the outside. When the sensor is to be used, the other end of the passage may be opened so as to provide an inlet for a sample.

Thus, the first sensor of the present invention has no inlet for a sample before use, so that the inside of the passage and the analyzing part are sealed to prevent contact with the outside. In the sensor in this embodiment, a substance that could interfere with measurement is prevented from entering the sensor, thereby resulting in excellent temporal stability of the electrodes or the reagent. In addition, the sensor of the present invention can be produced in a more simplified step than the step of packaging the sensors individually. Moreover, in use, when the end of the sensor where the end of the passage is positioned is cut off by a cutter or the like, the end of the passage can be opened easily so that the opening can serve as an inlet for a sample. The provision of the opening can be performed in a manner as simple as the conventional operation of opening the individual package of the sensor. When a cutter dedicated for this purpose is used, the opening can be provided more efficiently.

In one embodiment of the first sensor of the present invention, the passage is preferably a capillary passage, and an air vent in communication with the capillary passage is preferably formed when the sensor is to be used. When the passage is a capillary passage, the formation of an air vent strengthens the suction by the capillary phenomenon. Even if there is no air vent, a strong capillary phenomenon can occur in the passage, if there is a place such as an air reservoir to which the air in the capillary passage can escape.

The first sensors of the present invention are preferably used as a set where a plurality of sensors are integrated into one unit. The use of such a set of sensors improves the efficiency in replacement of the sensors.

A second sensor of the present invention includes a passage having two ends, an analyzing part and an inlet for a sample. One end of the passage is connected to the analyzing part. The other end of the passage constitutes the inlet for a sample. The inlet for a sample is closed with a sealing member before use so that the inside of the passage and the analyzing part are sealed to prevent contact with the outside. When the sensor is to be used, the sealing member is removed so as to expose the inlet for a sample.

Thus, in the second sensor of the present invention, the inlet for a sample is closed with a sealing member before use so that the inside of the passage and the analyzing part are sealed to prevent contact with the outside. In the sensor in this embodiment, a substance that could interfere with measurement or could deteriorate the sensors is prevented from entering the sensor, thus resulting in excellent temporal stability of the electrodes or the reagent. In addition, the sensor of the present invention can be produced in more simplified steps than the production steps including the step of packaging the sensors individually. Moreover, in use, the sealing member may be removed so that the inlet for a sample can be exposed. The provision of the opening can be performed in a manner as simple as the conventional operation of opening the individual package of the sensor.

In the second sensor of the present invention, the passage is preferably a capillary passage for the same reason as described with reference to the first sensor. The second sensor preferably includes an air vent in communication with the capillary passage. The air vent is preferably closed with a sealing member before use. When the sensor is to be used, the sealing member is preferably removed so as to expose the air vent.

The second sensors of the present invention are preferably used as a set where a plurality of sensors are integrated into one unit for the same reason as described with reference to the first sensor.

In the first and the second sensors, in the case of electrochemical sensors, at least an active electrode and a counter electrode are generally arranged in the analyzing part. In the case of optical sensors, a reagent that effects an optical change when reacting with a sample is arranged in the analyzing part.

As described above, in these embodiments of the sensor and the set of the sensors of the present invention, the passage and the analyzing part are sealed from the outside. Therefore, without packaging the sensors individually, a substance that could interfere with measurement can be prevented from entering the sensors, thus resulting in excellent temporal stability of the electrodes or the reagent. In addition, the operability of the sensor can be improved. Moreover, the sensor in these embodiments can be produced in a simplified manner. In addition, the step of packaging the sensors individually can be eliminated, so that the production efficiency can be higher than that of conventional sensors.

These and other advantages of the present invention will become apparent to those skilled in the art upon reading and understanding the following detailed description with reference to the accompanying figures.

DESCRIPTION OF THE PREFERRED EMBODIMENTS

Hereinafter, the sensor of the present invention will be described by way of examples with reference to the accompanying drawings.

EXAMPLE 1

Figure 1A:
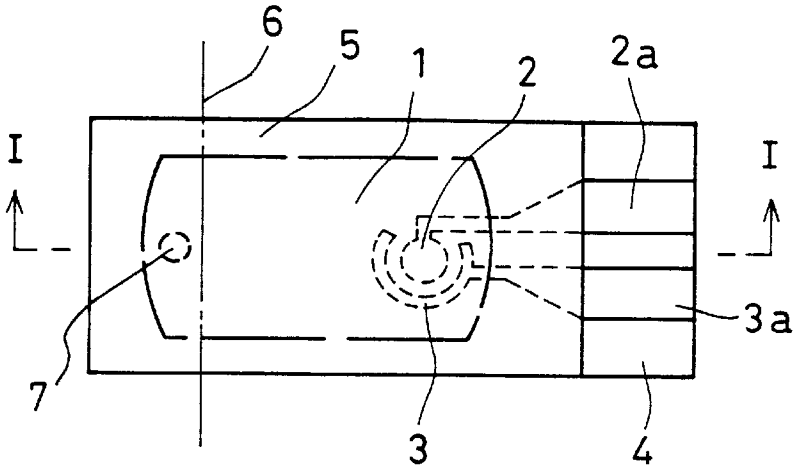
FIG. 1A is a plan view showing an example of a sensor of the present invention.
Figure 1B:
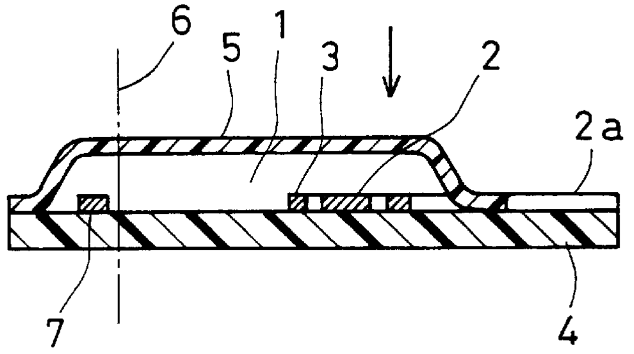
FIGS. 1B and 1C are cross-sectional views showing the sensor shown in FIG. 1A.
Figure 1C:
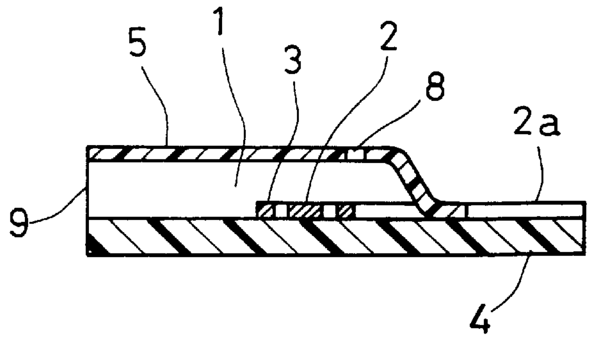

FIGS. 1A through 1C show an example of a first sensor of the present invention. FIG. 1A is a plan view showing an example of the first sensor before use. FIG. 1B is a cross-sectional view of the first sensor taken along line I—I of FIG. 1A. Figure 1C is a cross-sectional view showing an example of the first sensor in use. In FIGS. 1A through 1C, the same parts bear the same reference numerals.

As shown in FIGS. 1A and 1B, the first sensor is an electrochemical sensor. More specifically, an active electrode 2 and a counter electrode 3 are arranged substantially in the center of a rectangular substrate 4. A reagent (not shown) that causes an electrochemical change upon reaction with a sample is arranged on the electrodes 2 and 3. This part constitutes an analyzing part. The ends of the active electrode 2 and the counter electrode 3 extend toward one end of the substrate 4 (the right end in FIG. 1A) so as to constitute an active electrode terminal 2*a* and a counter electrode terminal 3*a*. The entire surface except the terminals 2*a* and 3*a* is covered with a cover film 5. The edge of the cover film 5 is tightly attached to the substrate 4, but a gap is formed between the cover film 5 and the substrate 4 in the portion other than the edge of the cover film 5. This gap constitutes a capillary passage 1. The active electrode 2 and the counter electrode 3 are positioned in one end of the capillary passage 1 (the right end in FIG. 1A). A desiccant 7 may be arranged in the other end of the capillary passage 1 (the left end in FIG. 1A). The desiccant 7 can prevent the deterioration of the electrodes or the reagent. In FIGS. 1A and 1B, the sensor is cut along the dashed line 6, and an air vent 8 is opened at the position shown by the arrow in FIG. 1B.

In this sensor, which is an electrochemical sensor, the parts other than the electrodes are formed of an insulating material. For example, the substrate 4 can be formed of polyethylene terephthalate (PET), acrylonitrile-butadiene-styrene copolymer (ABS resin), polystyrene, nonyl, polyethylene, acrylic resin, vinylidene chloride resin or the like. Alternatively, the above-listed materials and other materials such as paper may be laminated so as to form the substrate 4. The cover film can be formed of a material as listed as the material for the substrate 4. Examples of the material for the cover film include PET, polyethylene, polyvinyl chloride or the like. In the sensor of the present invention, spacers may be placed between the substrate and the cover film, as described in Japanese Patent Publication No. 6-58338.

The electrodes 2 and 3 and the terminals thereof 2*a* and 3*a* can be formed of precious metal such as gold, silver and platinum, carbon or the like.

The sensor of the present invention can be produced in the following manner. First, the terminals 2*a* and 3*a* are screen printed on the substrate by using silver paste. The active electrode 2 and the counter electrode 3 are screen printed with conductive carbon paste. The shapes of the active electrode and the counter electrode are not limited to the shapes shown in FIG. 1A. The cover film 5 formed into a predetermined shape is placed on the substrate 4. Then, the edge of the cover film is attached to the substrate 4. Thus, the sensor shown in FIG. 1A can be produced. The attachment can be performed by using an adhesive or by pressing while heating (laminating). In the case of a sensor that electrically detects an electrochemical reaction between a sample and a reagent, the reagent is generally placed on the active electrode 2 and the counter electrode 3. A separately prepared reagent film may be used to be placed on the electrodes 2 and 3. Alternatively, a reagent layer may be formed directly on the electrodes 2 and 3. For example, a hydrophilic polymer aqueous solution may be applied onto the electrodes 2 and 3 and then dried. Then, a reagent solution may be applied thereto and dried. Thus, a reagent layer can be formed. A carboxymethyl-cellulose (CMC) aqueous solution can be used for the hydrophilic polymer aqueous solution. As for the reagent, for example, in the analysis of lactic acid, an aqueous solution of lactic acid oxidase and potassium ferricyanide can be used. In the analysis of glucose, glucose oxidase can be used, instead of lactic acid oxidase. In the analysis of cholesterol, cholesterol oxidase can be used, instead of lactic acid oxidase.

For example, gold or platinum electrodes can be used for measurement of an amount of hydrogen peroxide decreased or an amount of oxygen decreased in the detection of the results of the enzyme reaction. In a method in which a reaction is detected by a mediator, potassium ferricyanide, ferrocene or the like can be used as the mediator.

The size of the sensor before use shown in FIG. 1A is not particularly limited. Generally, the entire size is 3 to 50 mm in length, 3 to 10 mm in width, 0.2 to 2 mm in the maximum thickness, and 0.1 to 0.5 mm in the minimum thickness. The volume is about 0.5 to 10 $\mu$l.

Figure 2A:
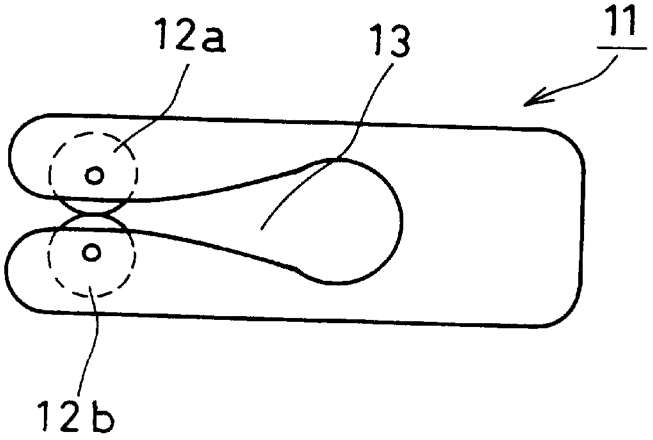
FIG. 2A is a plan view showing an example of a cutter for cutting the sensor of the present invention.
Figure 2B:
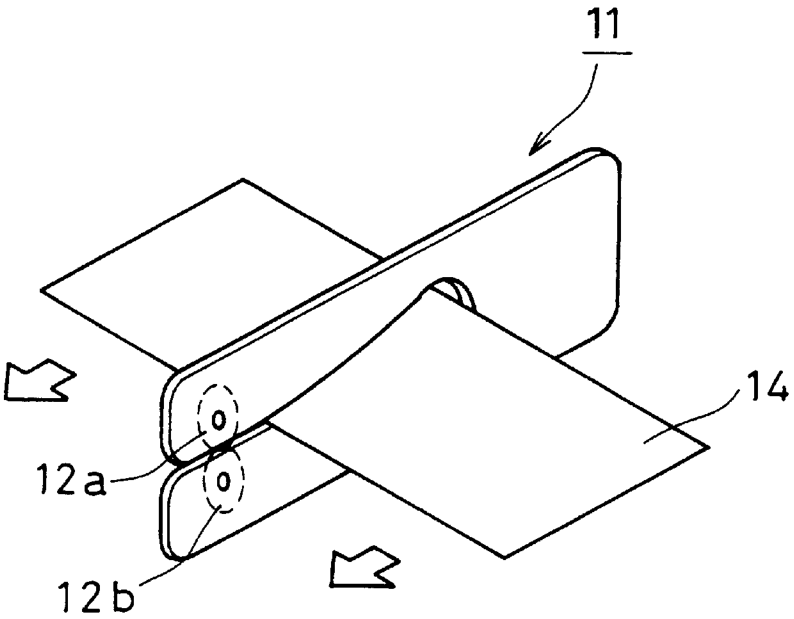
FIG. 2B is a perspective view showing an example where the cutter of FIG. 2A is cutting the sensor.

Next, as shown in FIG. 1C, the sensor is provided with an opening 9 to let in a sample by cutting the sensor at the position shown by the dashed line 6 of FIG. 1A. The sensor can be cut with an ordinary cutting tool such as scissors or a cutter. However, a cutter shown in FIGS. 2A and 2B, which is dedicated to serve this purpose, is preferably used. As shown in the plan view of FIG. 2A, the cutter 11 includes a pair of round blades 12*a* and 12*b* and a space 13 in which the sensor is inserted. As shown in FIG. 2B, the sensor 14 is inserted into the space 13 to be positioned in a cutting location, then moved in the direction shown by the arrow. Then, the round blades 12*a* and 12*b* cut the sensor 14. The cutting position is not particularly limited, as long as an opening for letting in a sample can be provided in the sensor. However, it is preferable to cut the sensor in a position that allows a capillary passage to have a suitable length when a capillary passage is formed. This is because an excessively short capillary passage prevents the expression of the capillary phenomenon. Furthermore, it is preferable to form an air vent 8 at the time of this cutting. When the cover film is formed of resin, the air vent 8 can be formed by piercing the cover film with a needle or the like. It is preferable to heat the needle before piercing. The heated needle can easily form the air vent 8 simply by being contacted with the cover film, and this method of forming the air vent 8 hardly causes a change in the volume of the analyzing part or the passage.

The thus produced sensor provided with the sample inlet 9 can be used in the same manner as an ordinary sensor. For example, a sample such as blood is contacted with the sample inlet 9, the capillary phenomenon allows the sample to be introduced into the analyzing part where the electrodes 2 and 3 are positioned. Then, the sensor is positioned in a measuring device so that predetermined test items are measured.

In this example, an electrochemical sensor has been described. In an optical sensor, the electrodes for the analyzing part in the electrochemical sensor are replaced by a reagent that effects an optical change upon reaction with a sample. The configuration and the material for the optical sensor are the same as those of the electrochemical sensor, for example, except that the portion of the sensor that is irradiated with light (which is transmissive, if necessary) is transparent. The reagent that effects an optical change upon reaction with a sample can be suitably selected in accordance with the test item. Examples of such a reagent include a reagent obtained by combining a color-developing substrate and peroxidase (POD). The reagent can be placed on the analyzing part in the same manner as in the case of the electrochemical sensor. Furthermore, PET, an acrylic resin or the like can be used as a transparent material for the substrate and the cover film.

Figure 3A:
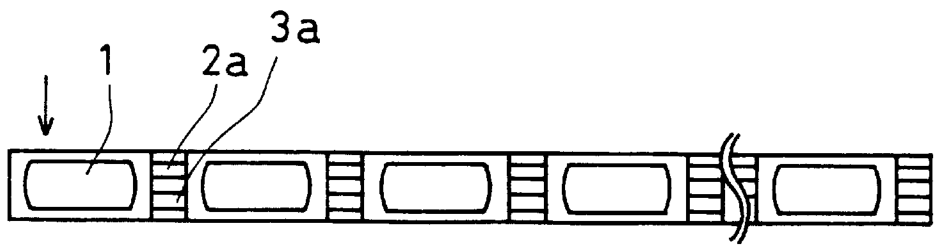
FIGS. 3A to 3C are plan views showing an example of a set of of the present invention.
Figure 3B:
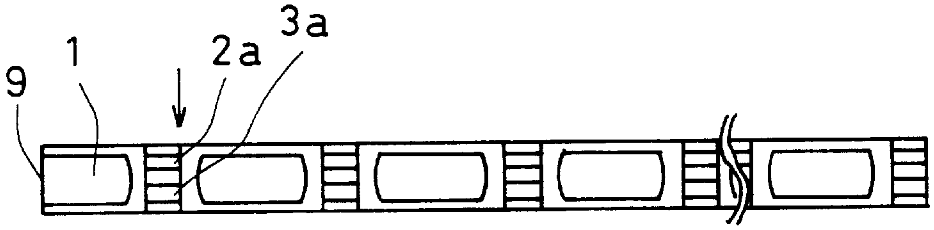
Figure 3C:
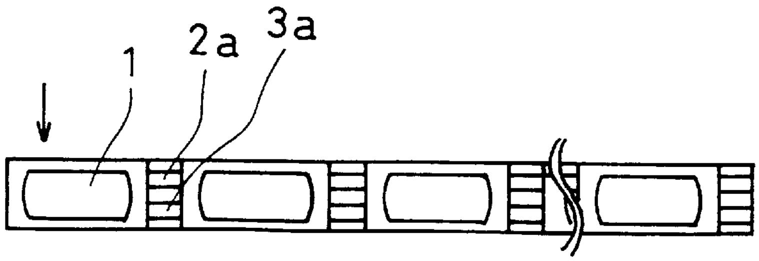

Next, FIGS. 3A to 3C are plan views showing a set of sensors, each of which is as shown in FIGS. 1A to 1C. In FIGS. 3A to 3C, the same parts as in FIGS. 1A to 1C bear the same reference numerals. FIG. 3A shows a set of sensors before use. As shown in FIG. 3A, the set of sensors is formed by aligning the sensors of FIG. 1A in the longitudinal direction so that the sensors are integrated, and the substrate is continuous. The arrow in FIG. 3A shows a position at which the sensor is cut so as to form an inlet for a sample. This set of sensors is generally positioned in a measuring device. Every time a test is carried out, the sensor is cut with a cutter provided in the measuring device so as to form a sample inlet, and the used sensor is disposed of. Japanese Laid-Open Patent Publication No. 7-167820 discloses an example of the measuring device including the cutter therein, which can be used in the present invention. Furthermore, the electrode terminals 2*a* and 3*a* are exposed so as to be connected to the terminals of the measuring device. The electrodes of an individual sensor may be independent from each other. Alternatively, the electrodes and the terminals may be integrated, and the electrodes are continuously linear and shared by a plurality of sensors, as in the sensor disclosed in Japanese Laid-Open Patent Publication No. 7-167820. This is advantageous in the production.

The length of the sensor is suitably determined by the number of the sensors that are to be arranged. The sizes other than the length are the same as those of the sensor of FIG. 1A. This set of sensors can be produced by forming a plurality pairs of electrodes on one belt-shaped substrate and attaching a cover film for each sensor in the same manner as described above.

This set of sensors is used, for example in the following manner. First, the set of sensors shown in FIG. 3A is positioned in a measuring device. In use, a sensor is cut at the position shown by the arrow in FIG. 3A with a cutter provided in the measuring device or the like, so that a sample inlet is formed, as shown in FIG. 3B. Then, a sample such as blood is introduced from the sample inlet to the analyzing part so as to measure the sample, as described above. After measurement, the sensor is cut off at the position shown by the arrow in FIG. 3B so as to obtain a set of sensors shown in FIG. 3C. The set of sensors shown in FIG. 3C is provided with no opening so that the capillary passage and the analyzing part are sealed from the outside. Then, when a next test is carried out, another sensor is cut in the same position as that shown by the arrow in FIG. 3A, so that the sensor is provided with a sample inlet.

The use of such a set of the sensors of the present invention facilitates the replacement of the sensors so that measurement operations are simplified. In addition, a large number of samples are treated quickly and easily.

A set of optical sensors has the same configuration as that of the electrochemical sensor, except that a predetermined reagent is arranged instead of the electrodes, and a predetermined portion can be observed from outside by making the portion transparent or the like.

EXAMPLE 2

Next, a second sensor of the present invention will be described with reference to FIGS. 4A, 4B and 5A, 5B. FIG.

Figure 4A:
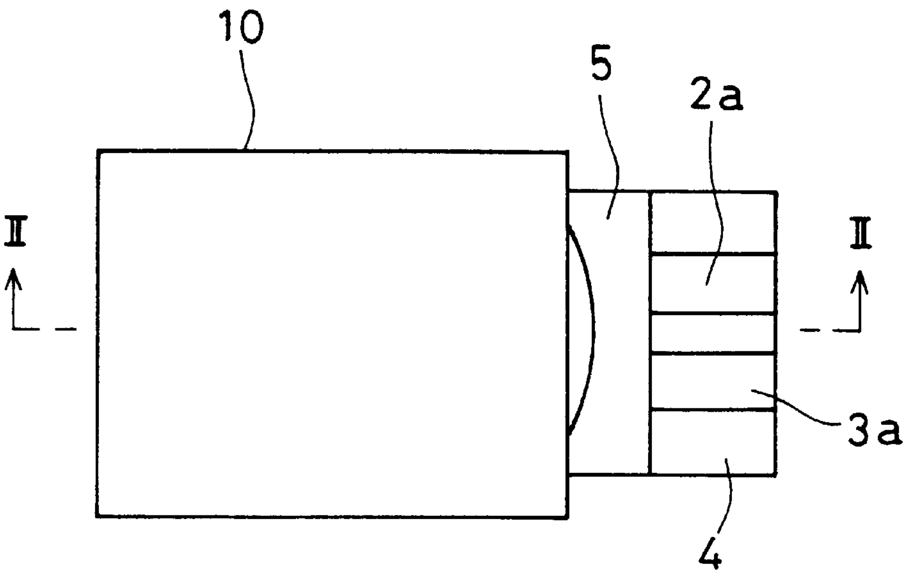
FIG. 4A is a plan view showing another example of a sensor of the present invention before use.
Figure 4B:
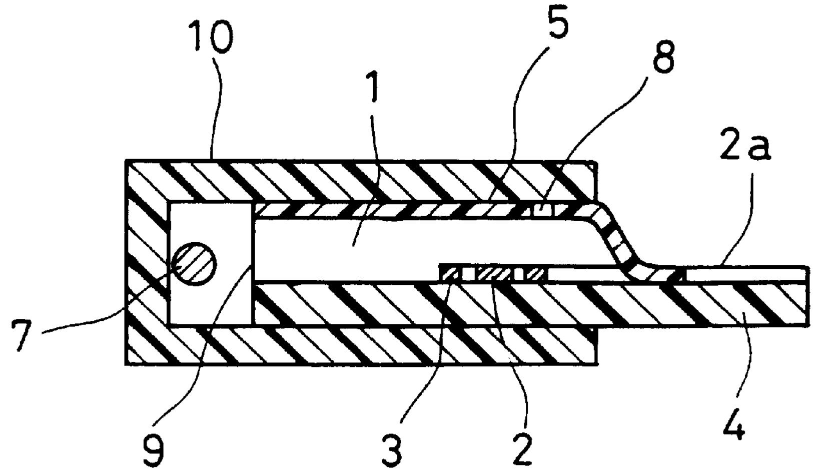
FIG. 4B is a cross-sectional view showing the sensor shown in FIG. 4A.
Figure 5A:
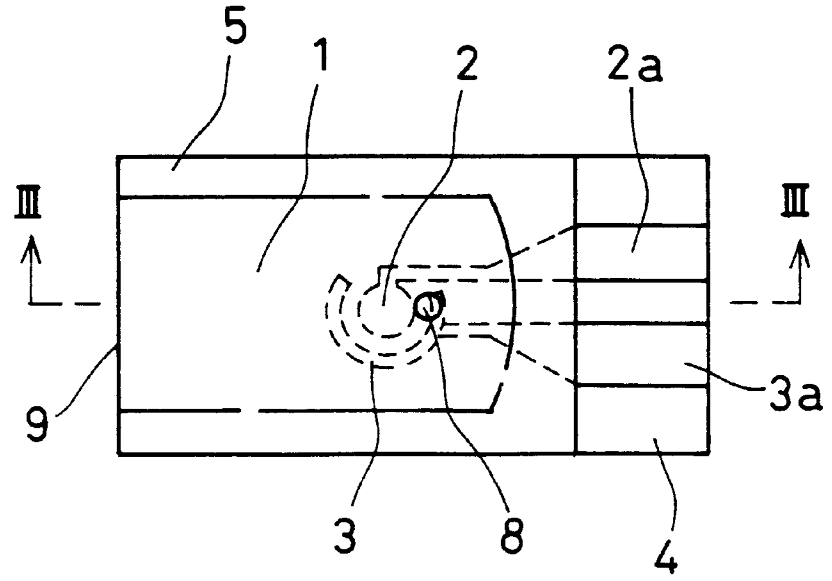
FIG. 5A is a plan view showing the sensor of FIG. 4A in use.
Figure 5B:
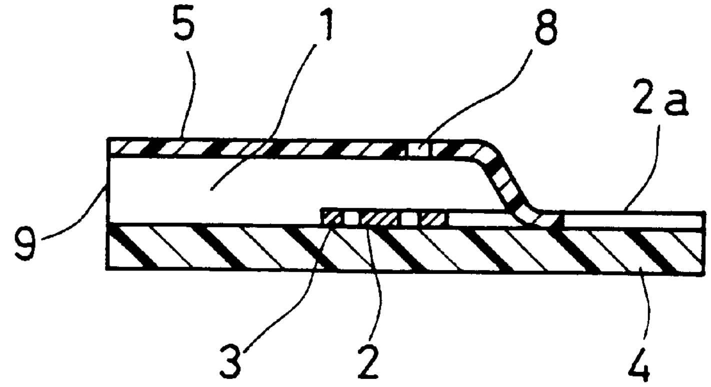
FIG. 5B is a cross-sectional view showing the sensor shown in FIG. 5A.

4A is a plan view showing a sensor before use, and FIG. 4B is a cross-sectional view of the sensor taken along line II—II of FIG. 4A. FIG. 5A is a plan view showing a sensor in use, and FIG. 5B is a cross-sectional view of the sensor taken along line III—III of FIG. 5A. In these figures, the same parts bear the same reference numerals. The sensor shown in these figures is obtained by partially covering the sensor in use of Example 1 (see FIG. 1C) with a cap.

More specifically, as shown in FIGS. 4A, a cap 10 covers the sample inlet 9 and the air vent 8 of the sensor before use so that the capillary passage 1 and the analyzing part (where the electrodes 2 and 3 are positioned) are sealed from the outside. Furthermore, a desiccant 7 may be placed at an inner part of the cap 10.

The shape, size and material of the sensor are not particularly limited, as long as the cap 10 can seal the sample inlet 9 and the air vent 8. For example, the inner shape of the cap shown in FIGS. 4A and 4B is substantially a hexahedron. The size of the cap is suitably determined by the size of the sensor. The minimum size of the inner shape is generally about 1.5 mm in depth, about 3 mm in width and about 0.2 mm in height. Furthermore, the cap can be formed of any resin that is listed above as a material for the substrate or the cover film. Among them, chlorinated polyethylene, butadiene resin or the like, which have elasticity, are preferable.

The configuration, size, material or the like of the sensor except for the provision of the cap are the same as those of the sensor in Example 1. The relationship between the electrochemical sensor and an optical sensor configured according to Example 2 is the same as that in Example 1. A method for producing the sensor of Example 2 is the same as that of Example 1, except that the sample inlet 9 and the air vent 8 are formed beforehand.

The cap is provided in the sensor in Example 2 before use. When the sensor is to be used, the cap is removed, as shown in FIGS. 5A and 5B. Thereafter, the sensor can be used in the same manner as in Example 1.

Figure 6A:
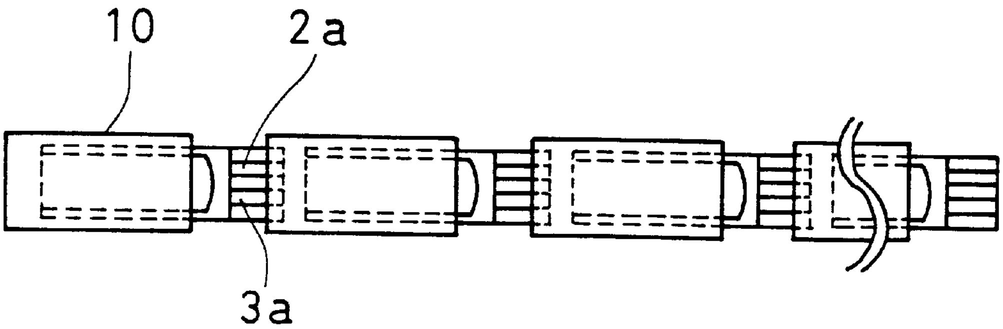
FIGS. 6A to 6C are plan views showing a set of the sensors of FIG. 4A of the present invention.
Figure 6B:
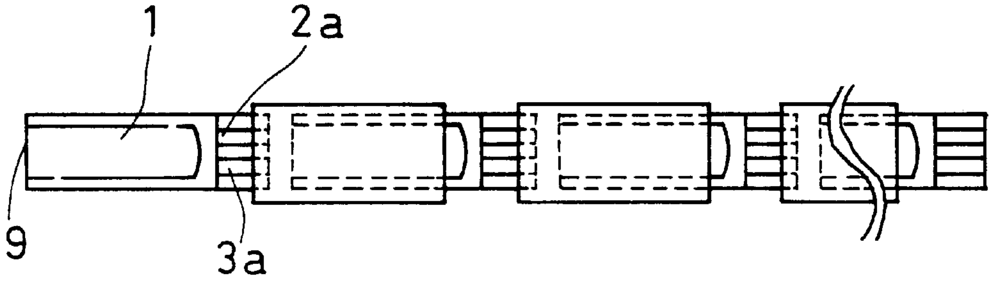
Figure 6C:
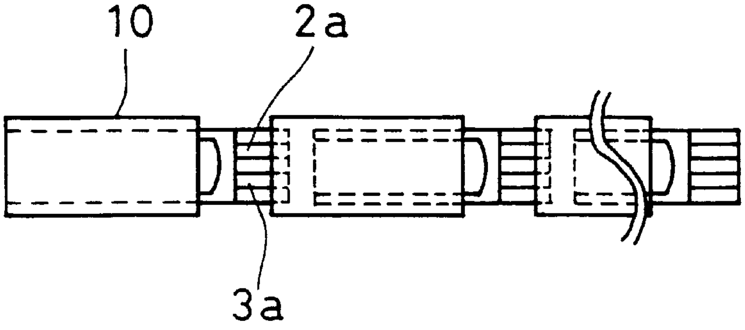

FIGS. 6A to 6C are plan views showing a set of the sensors, each one of which is as shown in FIGS. 4A, 4B and 5A and 5B. In these figures, the same parts bear the same reference numerals. As shown in FIG. 6A, in the set of the sensors, the cap 10 has two recesses. One of the recesses is deep so that the portion on the side of the sample inlet of the sensor is inserted and engaged therein. The other recess is shallow so that the portion on the side of the terminals 2*a* and 3*a* of the sensor is inserted and engaged therein. Thus, the sensors are arranged in a line in the longitudinal direction via the caps so as to be integrated. This set of sensors is generally positioned in a measuring device for use.

The length of the set of sensors is suitably determined by the number of the sensors that are to be arranged, and other sizes are the same as those of the sensor shown in FIGS. 4A, 4B and 5A, 5B.

This set of sensors can be used, for example in the following manner. First, the set of sensors shown in FIG. 6A is positioned in a measuring device. Then, the cap 10 is removed for use while the sample inlet portion at one end of the sensor protrudes from the measuring device, so that the sample inlet is exposed, as shown in FIG. 6B. Then, as described above, a sample such as blood is introduced from the sample inlet to the analyzing part for measurement. After the measurement, the used sensor is removed from a next cap so as to obtain the sensors shown in FIG. 6C. This set of sensors, which is provided with no sample inlets nor air vents, has the same state as an unused sensor so that the capillary passage and the analyzing part are sealed from the outside. When a next test is to be carried out, the cap of a next sensor is removed so as to provide a sample inlet again.

The use of the set of sensors of the present invention facilitates the replacement of the sensors so that the operability can be improved.

As described in Example 1, a set of optical sensors has the same configuration as that of the electrochemical sensor, except that a predetermined reagent is arranged, instead of the electrodes, and that a predetermined portion can be observed from outside by making the portion transparent or the like.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A sensor comprising an analyzing part and a passage having two ends, one end of the passage being connected to the analyzing part, wherein the other end of the passage is closed before use so that an inside of the passage and the analyzing part are sealed to prevent contact with the outside, and said other end of the passage being openable so as to provide an inlet for a sample when the sensor is to be used.

2. The sensor according to claim 1, wherein the passage is a capillary passage, and an air vent in communication with the capillary passage is formed when the sensor is to be used.

3. The sensor according to claim 1, wherein at least an active electrode and a counter electrode are arranged in the analyzing part.

4. The sensor according to claim 1, wherein a reagent that effects an optical change when reacting with a sample is arranged in the analyzing part.

5. A set of sensors comprising a plurality of sensors, each one of which includes an analyzing part and a passage having two ends, one end of the passage being connected to the analyzing part, wherein the other end of the passage is closed before use so that an inside of the passage and the analyzing part are sealed to prevent contact with the outside, said other end of the passage being openable so as to provide an inlet for a sample when the sensor is to be used, wherein the plurality of sensors are integrated into one unit.

6. The set of sensors according to claim 5, wherein the plurality of sensors are formed on one substrate.

7. A sensor comprising a passage having two ends, an analyzing part and an inlet for a sample, one end of the passage being connected to the analyzing part, the other end of the passage constituting the inlet for a sample, wherein the inlet for a sample is closed with a sealing member before use so that an inside of the passage and the analyzing part are sealed to prevent contact with the outside, and the sealing member being removable so as to expose the inlet for a sample when the sensor is to be used.

8. The sensor according to claim 7, wherein the passage is a capillary passage, the sensor includes an air vent in communication with the capillary passage, the air vent is closed with a sealing member before use, and the sealing member being removable so as to expose the air vent when the sensor is to be used.

9. The sensor according to claim 7, wherein at least an active electrode and a counter electrode are arranged in the analyzing part.

10. The sensor according to claim 7, wherein a reagent that effects an optical change when reacting with a sample is arranged in the analyzing part.

11. A set of sensors comprising a plurality of sensors, each one of which includes a passage having two ends, an analyzing part and an inlet for a sample, one end of the passage being connected to the analyzing part, the other end of the passage constituting the inlet for a sample, wherein the inlet for a sample is closed with a sealing member before use so that an inside of the passage and the analyzing part are sealed to prevent contact with the outside, the sealing member being removable so as to expose the inlet for a sample when the sensor is to be used, wherein the plurality of sensors are integrated into one unit.

12. The set of sensors according to claim 11, wherein the sealing member has two recesses, a side of the inlet for a sample of the sensor being inserted and engaged in one of the recesses, and the side opposite to the inlet for a sample being inserted and engaged in the other recess, whereby a plurality of sensors are connected via the sealing members.

13. A method for providing a sensor comprising an analyzing part and a passage having two ends, one end of the passage being connected to the analyzing part, the other end of the passage being closed before use so that an inside of the passage and the analyzing part are sealed to prevent contact with the outside, the method comprising the steps of:

opening the end, and contacting the open end with a sample fluid to draw the fluid toward the analyzing part.

14. The method according to claim 13, wherein the passage is a capillary passage, and an air vent in communication with the capillary passage is formed when the sensor is to be used.

* * * * *